United States Patent

Bonnick et al.

Patent Number: 5,958,779
Date of Patent: Sep. 28, 1999

[54] COULOMETRIC ANALYSIS

[76] Inventors: David Macdonald Bonnick, 2 Woodbine Cottages Punnetts Town, Heathfield, East Sussex, United Kingdom, TN21 9DE; Stephen Dennison, 35 Eridge Drive, Crowborough, East Sussex, United Kingdom, Tn6 2TJ

[21] Appl. No.: 08/640,851
[22] PCT Filed: Nov. 8, 1994
[86] PCT No.: PCT/GB94/02453
    § 371 Date: Jun. 27, 1996
    § 102(e) Date: Jun. 27, 1996
[87] PCT Pub. No.: WO95/13534
    PCT Pub. Date: May 18, 1995

[30] Foreign Application Priority Data

Nov. 9, 1993 [GB] United Kingdom .................... 9323062

[51] Int. Cl.⁶ .................................................. G01N 35/08
[52] U.S. Cl. .................... 436/55; 436/151; 422/82.02; 204/409; 204/411; 204/412
[58] Field of Search ............... 422/82.01, 82.02; 436/50, 55, 150, 151; 204/400, 409, 411, 412, 229

[56] References Cited

U.S. PATENT DOCUMENTS 5,160,419  11/1992  Kageyama et al. ..................... 204/294

OTHER PUBLICATIONS

Harrar, J.E., "Analytical controlled–potential coulometry", Trends in Analytical Chemistry. vol. 6, No. 6, pp.152–157, Jun. 1987.

*Primary Examiner*—David A. Redding
*Attorney, Agent, or Firm*—Wolf, Greenfield & Sacks, P.C.

[57] ABSTRACT

A method and apparatus for determining the quantity of a substance in a solution. An exemplary embodiment of the method includes the step of introducing a first sample of the solution into a cavity in which a working electrode is located. A constant potential is applied between the working electrode and a reference electrode in electrical contact with the first sample until such time as the current through the working electrode has decayed to a minimum. The applied constant potential is maintained as the first sample of the solution is replaced by a second sample of the solution in a manner such that the cavity remains filled with solution during the replacement procedure. The applied constant potential is maintained until such time as the current through the working electrode has again decayed to a minimum, and the total amount of the charge passing through the working electrode subsequent to the introduction of the second sample into the cavity is determined.

13 Claims, 6 Drawing Sheets

COULOMETRIC ANALYSIS

BACKGROUND OF THE INVENTION

The present invention relates to coulometric analysis which may be used to determine the quantity of a substance in a sample.

Coulometry is a well known analytical technique which under ideal conditions allows the direct quantitative determination of the mass of a substance in an analyte without it being necessary to calibrate the analytical equipment against a standard. Coulometry relies upon the measurement of the amount of electrical charge required to deplete a solution of a substance to determine the amount of that substance initially in the solution. If the electron stoichiometry of a reaction of interest is known, and there are no competing reactions, it is possible to determine the mass of a substance of interest simply by integrating current flow at an appropriate potential over time. Generally, a potential is applied between a working electrode and a reference electrode immersed in the analyte, and current is supplied to the analyte from a counter electrode to balance the current through the working electrode. The counter electrode current is a measure of the rate of depletion of the analyte.

The use of conventional coulometry is limited as relatively long time periods are generally required for the completion of the reactions upon which the technique relies. The reactions require mass transfer through the analyte to the working electrode of the system. Mass transfer may be assisted by mechanical stirring, but reaction times are still not satisfactory for many potential applications.

A further problem which has been encountered with conventional coulometry when applied in the water treatment industry, for example, to the determination of disinfectant residuals such as chlorine, is the possibility of competing reactions occurring at the counter electrode, such competing reactions resulting in the generation for example of oxidants. In an attempt to overcome this problem, it is known to separate the counter electrode from the analyte by an ionically conducting medium such as a salt bridge, but nevertheless the problem has deterred potential users of coulometry techniques.

The problem of slow response due to the time taken for the completion of reactions can be reduced by applying conventional coulometry techniques with an electrochemical cell in which the analyte is in the form of a thin film. Unfortunately with such an arrangement currents are generated which are a function of the structure of the electrochemical cell rather than electrochemical processes occurring in the analyte. Such currents mask the faradaic currents relevant to coulometry.

SUMMARY OF THE INVENTION

According to the present invention there is provided a coulometric method for determining the quantity of a substance in a solution, wherein a first sample of the solution is introduced into a cavity in which a working electrode is located, a potential is applied between the working electrode and a reference electrode in electrical contact with the first sample until such time as the current through the working electrode has decayed to a minimum, the applied potential is maintained as the first sample of the solution is replaced by a second sample of the solution in a manner such that the cavity remains filled with solution during the replacement procedure, and the amount of charge passing through the working electrode subsequent to the introduction of the second sample into the cavity is determined.

The solution may be caused to flow intermittently through the cavity to enable replacement of one sample by another, the flow being generated by, for example, gravity or a pump.

The invention also provides a coulometric analyser for the determination of the quantity of a substance in a solution, comprising a working electrode located in a cavity, means for introducing a sample of the solution into the cavity, means for applying a potential between the working electrode and a reference electrode that is in electrical contact with the solution within the cavity, means for replacing a first sample of the solution within the cavity with a second sample of the solution such that the cavity remains filled with solution during the replacement procedure, and means for determining the amount of charge that passes through the working electrode subsequent to the introduction of the second sample into the cavity.

Preferably the cavity and working electrode are dimensioned such that all parts of the cavity are located within a distance of the working electrode of the order of the diffusion layer thickness for the stationary solution.

Preferably the distance is 0.015 cm or less.

The term "diffusion layer thickness" as used herein is defined by the following equation:

$$d^2 = 2Dt$$

where:

d is the diffusion layer thickness (also known as the Nernst diffusion layer thickness).

D is the diffusion coefficient of the reacting species (typically approximately $5 \times 10^{-6}$ cm$^2$ s$^{-1}$ for inorganic ions.

t is the elapsed time of electrolysis.

The above equation predicts the distance over which the diffusion layer extends as a function of time of electrolysis. The equation assumes that there are no complications due to the kinetics of the electrode reaction. This assumption is reasonable given a simple analyte, for example water containing chlorine residuals.

For a species with $D = 5 \times 10^{-6}$ cm$^2$ s$^{-1}$ and an electrolysis time of 10 seconds, the diffusion layer thickness is 0.01 cm. In that example, 10 seconds is not the time required for exhaustive or complete electrolysis, but inversion of the equation enables calculation of the time required for the diffusion layer to develop to a defined distance from the electrode surface. Thus, for a thin layer electrochemical cell with a cavity 0.01 cm thick, the diffusion layer would cover the whole thickness of the cavity within 10 seconds. Further electrolysis time would be required for exhaustive or complete consumption of the reacting species, but in the time taken for the diffusion layer to cover the whole thickness of the cavity the electrolysis process would have advanced sufficiently to enable an accurate coulometric analysis of the amount of reacting species in the sample.

The analyser may define an elongate rectangular section cavity, one side of which supports the working electrode. Alternatively the analyser may define a tubular cavity the inner wall of which defines the working electrode. The working electrode is preferably formed from a noble metal such as platinum.

Preferably the working electrode is located within a channel through which the solution is caused to flow, the working electrode being located in the channel such that it does not extend to at least an inlet end of the channel and preferably neither end of the channel.

Preferably the reference electrode and any other electrode, for example the counter-electrode, are located remote from the cavity to ensure that there is no interference with the working electrode current signal by products of the other electrode or electrodes.

BRIEF DESCRIPTION OF THE DRAWINGS

Embodiments of the present invention will now be described, by way of example, with reference to the accompanying drawings, in which.

DETAILED DESCRIPTION OF PREFERRED EMBODIMENTS

Figure 1:
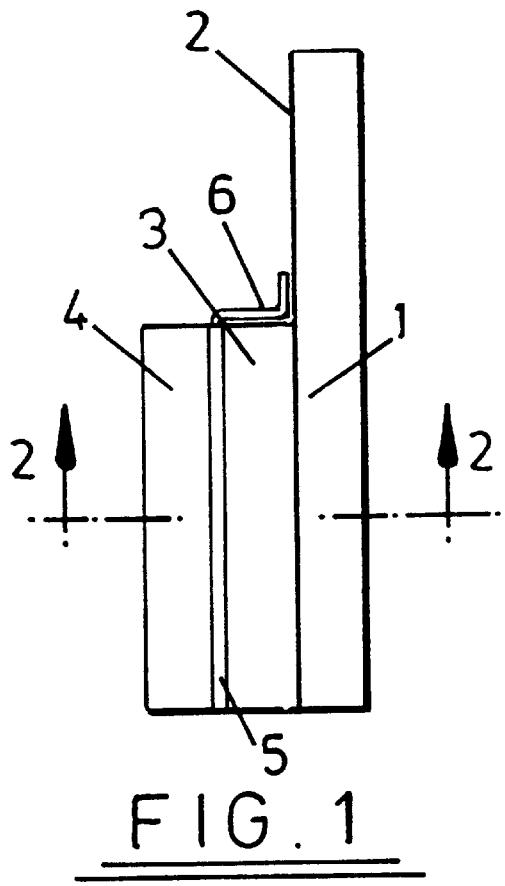
FIG. 1 is a side view of an experimental analyser structure in accordance with the present invention.
Figure 2:
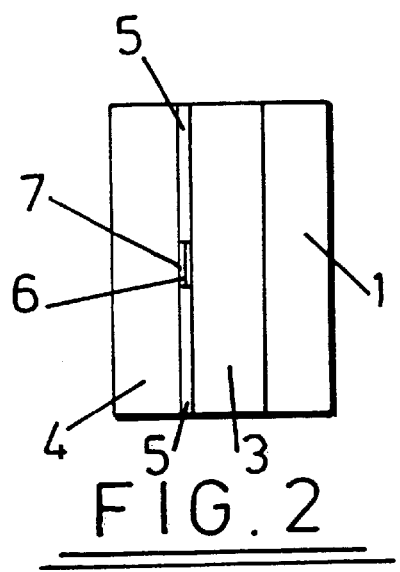
FIG. 2 is a section through FIG. 1 on the line 2—2.

Referring to FIGS. 1 and 2, the illustrated analyser structure comprises a glass support plate 1, a front face of which is coated with a layer 2 which is electrically conductive. An electrochemical cell is mounted on the front face of the plate 1, the electrochemical cell comprising a rear glass plate 3, a front glass plate 4, a pair of microscope cover slip spacers 5 sandwiched between the plates 3 and 4, and a platinum foil electrode 6. The electrode 6 is adhered to one face of the plate 3 in a gap 7 defined between the plates 3 and 4 and between the spacers 5. The gap 7 is of uniform width and extends for the full height of the plates 3 and 4 and the spacers 5. Thus an open channel of rectangular section extends for the full height of the plates 3 and 4. The foil 6 extends across the full height and width of the surface of the plate 3 which faces the space 7. The foil 6 extends vertically upwards out of the space 7, across the upper surface of the plate 3, and into contact with the electrically conductive coating 2 on the plate 1. The spacing between the plate 4 and the adjacent surface of the foil 6 is 0.01 cm.

Figure 3:
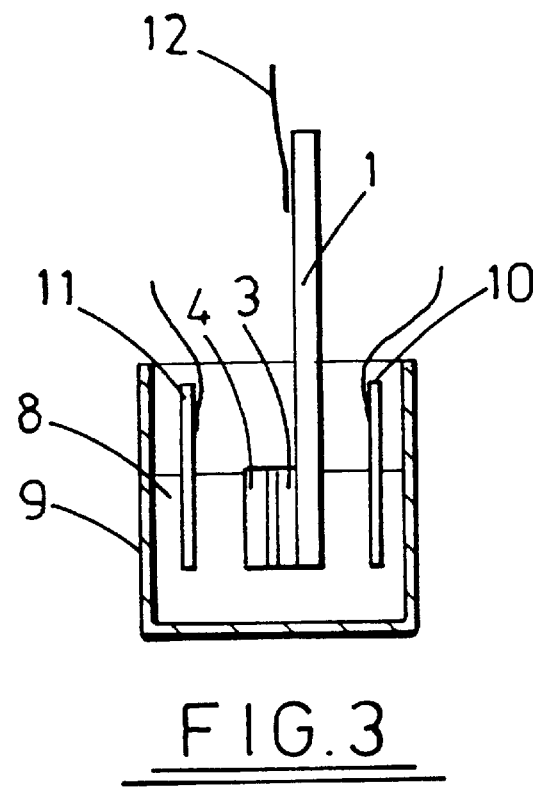
FIG. 3 schematically illustrates a coulometry system incorporating the analyser structure of FIGS. 1 and 2.
Figure 4:
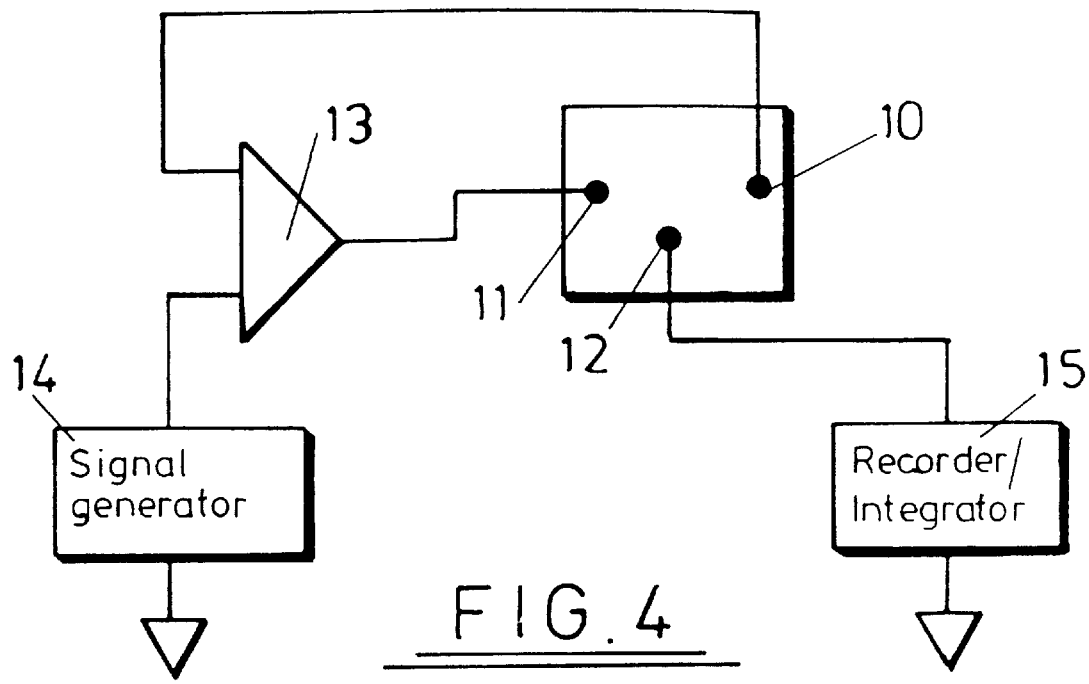
FIG. 4 is a schematic illustration of a circuit to which the analyser structure of FIGS. 1 and 2 may be connected.

Referring to FIGS. 3 and 4, the use of the analyser structure of FIGS. 1 and 2 will be described. A sample 8 of water is placed in a beaker 9. It is desired to analyse the quantity of chlorine residuals in the sample. The analyser structure of FIGS. 1 and 2 is immersed in the sample as are a reference electrode 10 and a counter electrode 11. A terminal 12 is connected to the conductive coating on the plate 1 so as to make electrical connection with the foil 6 supported in the analyser structure. Immersion of the analyser structure in the sample causes the rectangular section cell defined between the plates 4 and 3 to fill up with a predetermined volume of the sample. The reference electrode 10 is in the form of a glass plate coated with silver/silver chloride and the counter electrode is suitably supported platinum foil.

Figure 5:
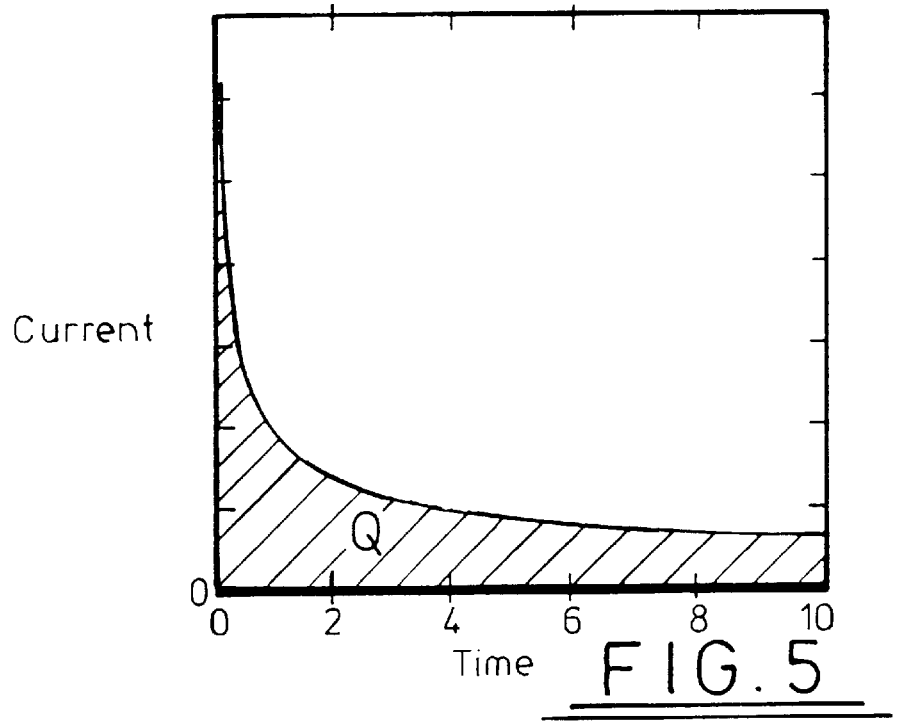
FIG. 5 illustrates the change in monitored current over time in the coulometry system described with reference to FIGS. 1 to 4.

As shown in FIG. 4, the counter electrode 11 is connected to the output of an operational amplifier 13, one input to which is derived from a signal generator 14 and the other input to which is derived from the reference electrode 10. The working electrode, that is the foil 6 of FIGS. 1 and 2, is connected via the terminal 12 to a recorder/integrator 15. A potential difference of from 0.18 to 0.4 volts is established between the reference and working electrodes and the potential of the counter electrode is controlled by the amplifier 13 to supply current to the cell at a rate sufficient to balance the current drawn from the terminal 12. The variation of that current with time is represented in FIG. 5, the current and its variation with time being recorded and integrated by the recorder/integrator 15.

Thus the coulometry is carried out potentiostatically. The potential range 0.18 to 0.4 volts is selected as it is appropriate for hypochlorous acid and hypoiodous acid and yet does not cause competing reactions resulting from the presence of dissolved oxygen in the sample. Of course, the invention may be applied to the measurement of the concentration of, for example, chlorine dioxide, ozone, sulphur dioxide and potassium permanganate using essentially the same procedures, but is exemplified in the case of hypochlorous acid and hypoiodous acid. The voltages quoted are appropriate to this example, given the illustrated apparatus. If a more negative potential was used, oxygen effects would mask the electrode reactions of interest. If a more positive range was used, oxides would be formed which again would mask the electrode reactions of interest.

The electrode reactions of interest are assumed to be as follows:

$$HOCl + 2e^- \rightarrow OH^- + Cl^- \qquad \text{i)}$$

$$HOI + 2e^- \rightarrow OH^- + I^- \qquad \text{ii)}$$

The mass of analyte may be determined from the total charge in coulombs (Q) which is obtained by integration of the current over time. Faraday's Laws of Electrolysis gives the mass of species reduced as follows:

$$m = Q/nF$$

where m=mass, n=number of electrons and F=Faraday's constant.

The concentration may be determined from the volume of analyte solution, that is the volumetric capacity of the electrolysis cell defined between the plates 3 and 4.

It would not be necessary to wait for complete electrolysis to be achieved as the current/time relationship could be analysed to enable an accurate prediction of the total charge Q from the shape of the initial portions of the current/time curve.

In the quoted example, where the electrochemical cell results in a layer of analyte 0.01 cm thick, the diffusion layer will include the whole thickness of the sample in approximately 10 seconds. Further electrolysis time would be required to achieve complete consumption of the reacting species, but 10 seconds would be sufficient to derive enough data to enable an accurate prediction of the total charge Q. Thus useful results can be derived very rapidly.

In the channel thickness was significantly larger than 0.01 cm, for example 0.05 cm, the time required for electrolysis to provide data from which the total charge Q can be accurately predicted would be substantially greater. Accordingly it is important that the channel thickness is as small as possible, preferably less than 0.015 cm.

The positioning of the reference and counter electrodes is not critical to the operation of the system. It is highly desirable, however, to position the reference and counter electrodes remote from the cavity to prevent products from the counter electrode affecting the working electrode current. As illustrated in FIG. 3, in the experimental system described the reference and counter electrodes were simply separately supported in the analyte solution. It would be possible, however, to support one or both of the reference and counter electrodes on components of the analyser structure, for example the plates 1 and 4.

As explained below in greater detail, when a potential is initially applied to the described analyser structure, the structure defines what is in effect a parallel plate capacitor. A current is generated as a result which initially is a function of the electrical characteristics of the structure and not of any chemical reactions which might be occurring in the structure. It is important to take account of such capacitive effects so as to avoid masking of the chemical currents of interest. This is achieved in accordance with the present invention by initially filling up the cell channel, applying the appropriate potentials, and then rapidly replacing the analyte within the channel by fresh analyte. Providing only currents arising after replacement of the analyte sample are analysed, capacitive effects are thereby avoided. The analyte in the cell channel can be replaced by any convenient means, for example using a syringe pump, or a pumping system which builds up a pressure over time which is rapidly released by periodic opening of a valve, or by use of a device as simple as a manual pipette.

In the structure of FIGS. 1 and 2, the electrode 6 extends for the full height of the space 7. It has been found that what are believed to be "end effects" can reduce the accuaracy of the system. When the cell channel has a fresh charge of solution pumped into it, those parts of the solution adjacent to the end of the channel into which the solution is pumped appear not to have the same characteristics as the remaining content of the channel, and accordingly the inlet end of the channel defines a "dead space". Such effects can be readily isolated, however, by the simple expedient of stopping the working electrode short of at least the inlet end of the channel, and preferably by stopping the working electrodes short of both ends of the channel. One such arrangement is illustrated in FIG. 6.

Figure 6:
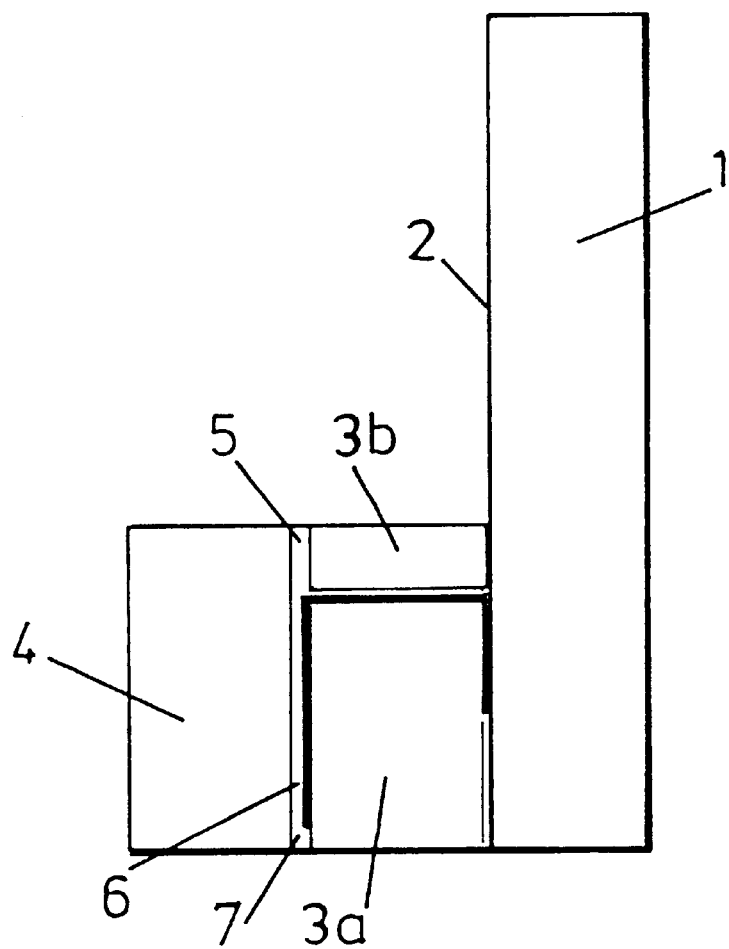
FIG. 6 is a schematic illustration of a second analyser structure similar to that of FIGS. 1 and 2.

Referring to FIG. 6, the same reference numerals are used where appropriate as were used in FIGS. 1 and 2. FIG. 6 is a vertical section through the structure, and shows that the intermediate plate is split into a lower plate 3a and an upper plate 3b. The foil working electrode 6 is secured to the plate 3a, extending over the top surface of that plate and down between the plates 1 and 3a. The plate 3a and the electrode 6 which it carries are secured to the conductive face 2 of the plate 1. The upper plate 3b is secured to the foil 6 so as to avoid leaving any open cavity between the plates 3a and 3b. It may be seen that with this arrangement the foil 6 does not extend to the top of the space 7.

Figure 7:
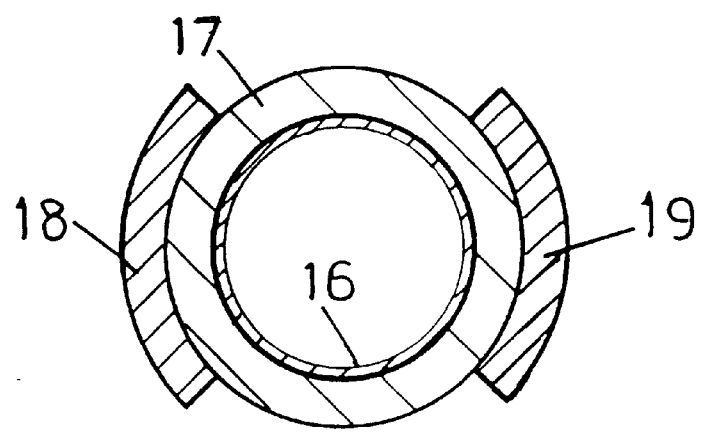
FIG. 7 is a section through a third analyser structure in accordance with the present invention.

It will be appreciated that the dimensions of the cell channel are critical to the speed of response of the system. Alternative configurations to the simple rectangular arrangements illustrated in FIGS. 1, 2 and 6 can be envisaged. For example, as illustrated in FIG. 7, the analyser structure could comprise a thin walled platinum tube 16 located within an insulating sheath 17. The internal diameter of the tube 16 could be 0.01 cm or less. Such a structure would give faster reaction times than the parallel plate arrangement of FIGS. 1 and 2, assuming similar dimensions, given that with an internal diameter of 0.01 cm no part of the analyte sample would be more than 0.005 cm from the working electrode 16. As shown in FIG. 6, the insulating sheath 17 could support conductive layers 18 and 19 which could serve respectively as the counter and reference electrodes in an electrical circuit of the type illustrated in FIG. 4.

Referring to FIGS. 8 to 11, a further embodiment of the invention and its performance will be described. The illustrated structure comprises an alumina substrate 20 onto which an elongate silver reference electrode 21, an elongate silver counter electrode 22 and a platinum electrode are screen printed. The platinum electrode has a working electrode portion 23, a contact portion 24 and a connecting portion 25 electrically connecting portions 23 and 24. An insulating layer 26 of dielectric is deposited over the electrodes, and strips of dielectric 27 and 28 are deposited on either side of the working electrode portion 23, the dielectric 28 extending over the connecting portion 25 of the platinum electrode. An alumina top plate 29 is adhered to the dielectric strips 27 and 28 so as to define an open-ended channel 30 on one side of which the working electrode is located, the height of the channel from the side on which the working electrode in located being 0.01 cm.

In use, the assembly is located so that the channel extends vertically and the assembly is partially immersed in a solution to be analysed such that the surface of the solution is located at the level indicated by the broken line 31. It will be noted that the counter and reference electrodes are then in electrical contact with the solution outside the channel. The working electrode 23 will be wholly immersed in the solution, capillary action causing the solution to substantially fill the channel. Appropriate electrical connections are made to a circuit as described with reference to FIG. 4 through the portions of the electrodes above the dielectric layer 26.

A potential is then applied between electrodes 21 and 24, thus establishing a potential difference between the solution adjacent the lower end of the reference electrode and the solution in the channel adjacent the working electrode. The potential may be approximately 0.05 volts.

Figure 9:
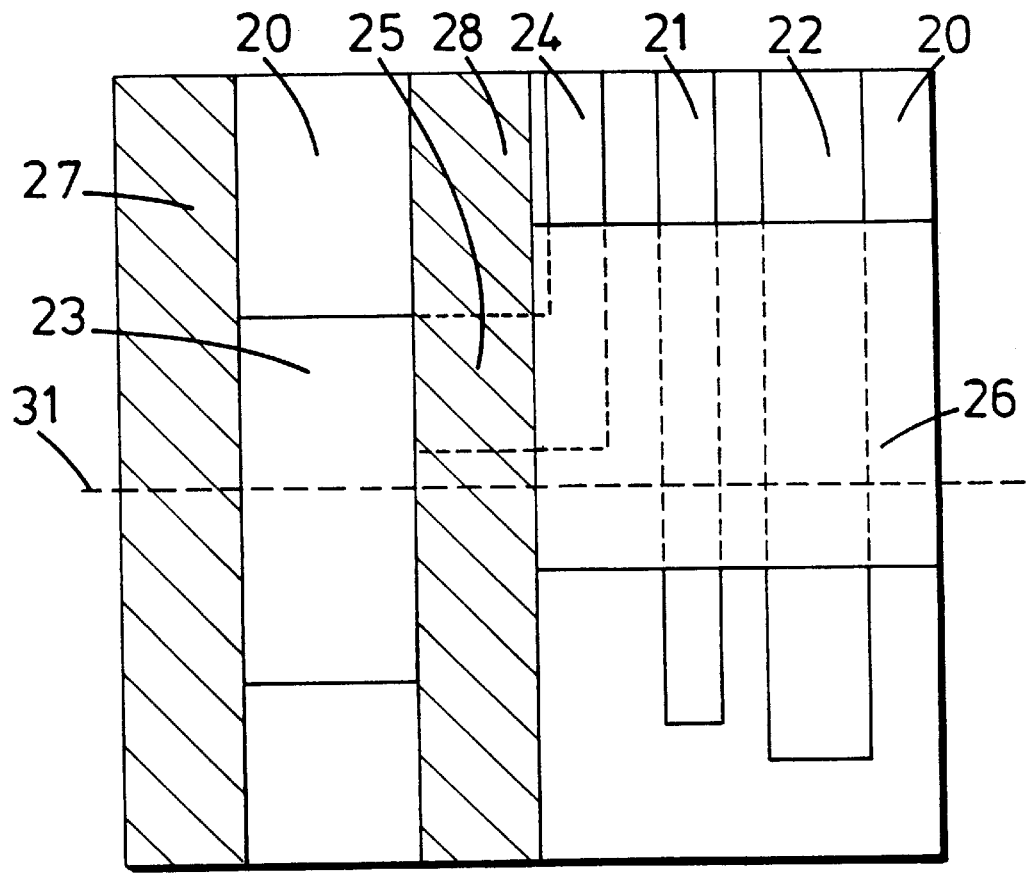
FIG. 9 is a section on the line 9—9 of FIG. 8.
Figure 10:
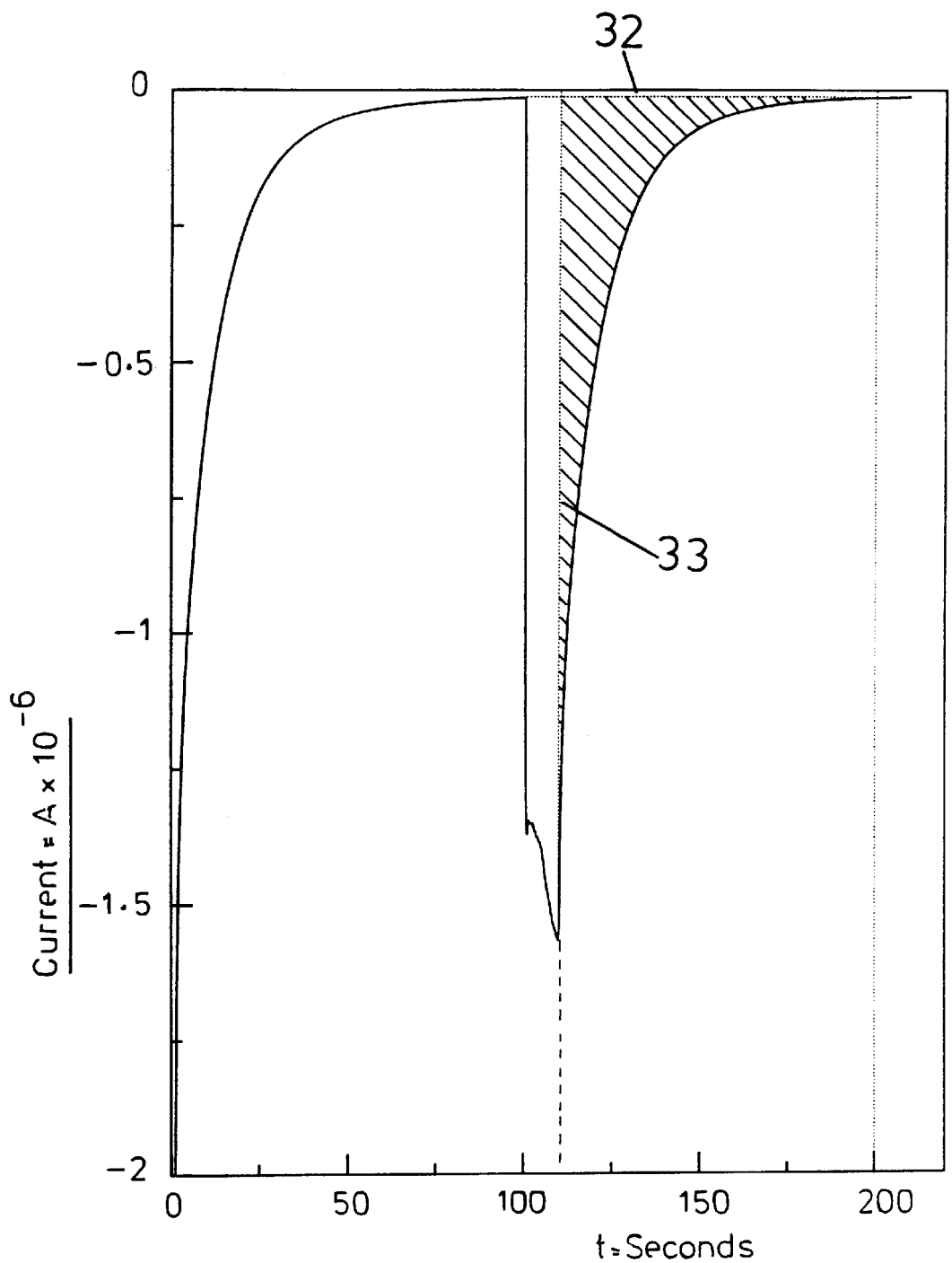
FIG. 10 is a detailed plot of current against time in the structure of FIGS. 8 and 9.

Referring to FIG. 10, the potential is applied at time t=0, and the current drawn through the counter electrode 22 is initially relatively large but rapidly decays to a residual value indicated by line 32 at time t=100 seconds. This initial current includes faradaic current which is indicative of electrochemical activity within the channel and current resulting from the structure of the assembly described in FIGS. 8 and 9. At time t=100, without removing the potential applied to the electrodes, the solution within the channel is replaced by a fresh sample of the solution, for example by pumping solution through the channel, or by simply causing fresh solution to flow into the channel under the influence of gravity. The flow is terminated at time t=110 seconds, as indicated by line 33 in FIG. 10. The counter electrode current again decays towards the level indicated by line 32, the area between the curve and lines 32 and 33 representing the total flow of charge required to deplete the solution. This is measured by integrating the current signal over a period of 90 seconds after the flow of solution ceases. Further samples can thus be analysed at 100 second intervals.

Figure 11:
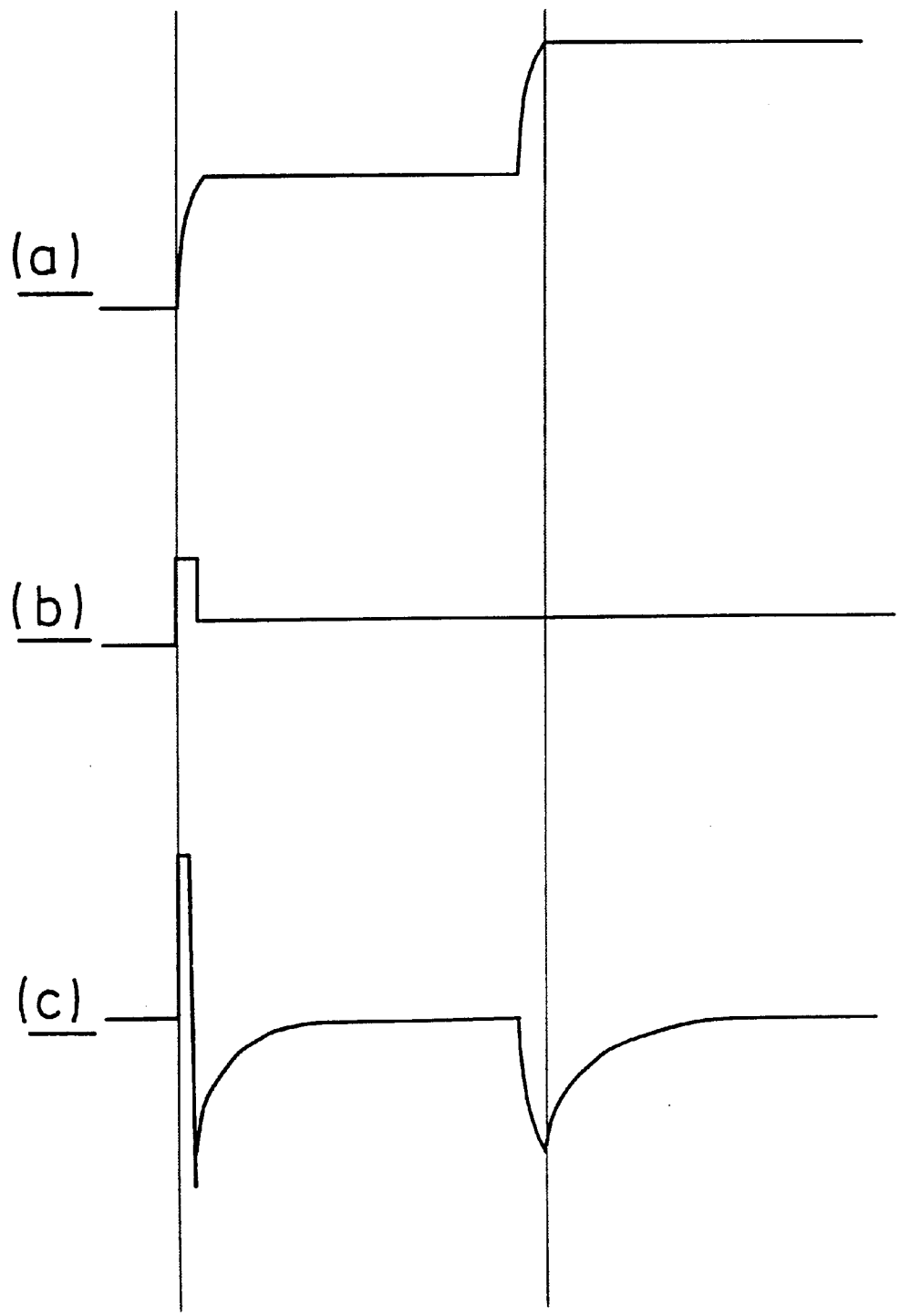
FIGS. 11a, 11b and 11c represent the relationship between flow, potential and current versus time in the structure of FIGS. 8 and 9.

FIG. 11 shows waveforms schematically representing the relationship between solution flow (curve a), applied potential (curve b) and current (curve c). Thus it can be seen that the potential is applied continuously during the replacement of one sample of solution by another, thereby enabling faradaic current to be isolated from current resulting from structural features, e.g. capacitive effects.

Figure 8:
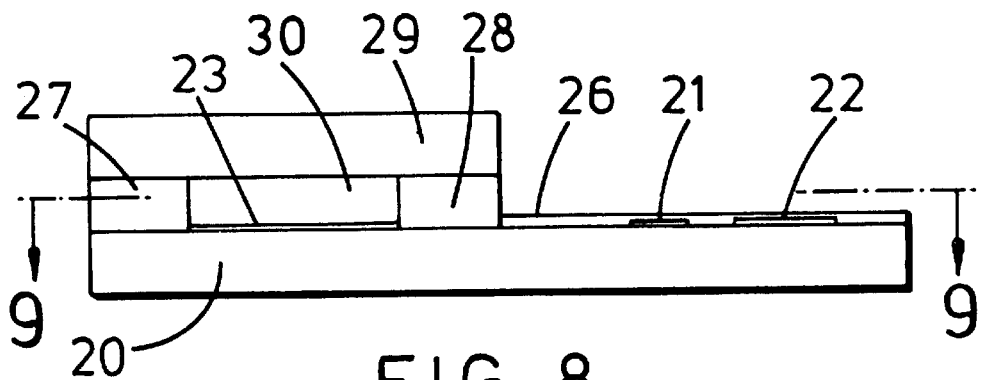
FIG. 8 is an end view of a fourth analyser structure in accordance with the present invention.

In the structure illustrated in FIGS. 8 and 9, the platinum working electrode 23 is located in a rectangular section channel which is open at both ends. Such an arrangement is convenient for delivering liquid to the channel by gravity flow. Alternative structures are possible, however. For example, the upper end of the channel as shown in FIG. 9 may be closed by joining the upper ends of the strips of dielectric 27, 28 with a further strip of dielectric. The working electrode is thus located part way along a blind bore open at its lower end. A small hole is formed through the top plate 29 to communicate with the channel above the working electrode, and a suction device is connected to the hole to enable the liquid in the channel to be changed by sucking liquid up the channel. It has been found that with such an arrangement the time required to achieve steady currents prior to the replacement of one sample by another is relatively short.

In all of the described embodiments, depending on the acidity and conductivity of the sample, preparation of the analyte before analysis may be unnecessary, as $OCl^-$ will convert to HOCl following the equilibrium:

$$HOCl \rightleftharpoons OCl^- + H^+$$

as the HOCl is reduced. If necessary, however, the analyte could be prepared for analysis. For the analysis of free chlorine residuals, the sample would be buffered to convert all species to hypochlorous acid. For total chlorine analysis, the sample would be buffered and would have added to it an excess of potassium iodide.

It will be appreciated that the devices described above could be used to provide a "titration" method to give standardised measurements, or as a detector for a flow injection analysis system for disinfectant residuals. Thus the invention may be used for simple manually-conducted analysis of samples or for automatic analysis, for example in online water treatment control systems.

In the described arrangements, the counter and reference electrodes are not separated from the analyte. Such separation would be unnecessary if the analyte solution pH and conductivity permit direct contact between the reference and counter electrodes and the solution. Alternatively, however, it would be possible to separate the counter and reference electrodes from the analyte by appropriate ionically conducting junctions.

Although ideally to avoid capacitive effects a system will be provided for rapidly pumping analyte through the cell channel, it will be appreciated that given appropriate channel dimensions the channel may be filled by capillary action.

It may be advantageous to vibrate the structure ultrasonically to increase the speed of response, but in most circumstances this will not be necessary.

We claim:

1. A coulometric method for determining the quantity of a substance in a solution, wherein a first sample of the solution is introduced into a cavity in which a working electrode is located, a constant potential is applied between the working electrode and a reference electrode in electrical contact with the first sample until such time as the current through the working electrode has decayed to a minimum, the applied constant potential is maintained as the first sample of the solution is replaced by a second sample of the solution in a manner such that the cavity remains filled with solution during the replacement procedure, the applied constant potential is maintained until such time as the current through the working electrode has again decayed to a minimum, and the total amount of the charge passing through the working electrode subsequent to the introduction of the second sample into the cavity as the current through the working electrode again decays to a minimum is determined.

2. A method according to claim 1, wherein a counter electrode is arranged in electrical contact with the samples, current is passed through the counter electrode to balance the current through the working electrode, and the total amount of charge passing through the working electrode is determined by integration of a measurement of the current through the counter electrode.

3. A method according to claim 1, wherein the solution is caused to flow intermittently through the cavity to enable the replacement of one sample of the solution by another.

4. A method according to claim 3, wherein the solution flow is effected by gravity.

5. A coulometric analyser for the determination of the quantity of a substance in a solution, comprising a reference electrode, a counter electrode, and a working electrode, the counter electrode being electrically coupled to an amplifier output, the reference electrode being electrically coupled to an amplifier input, and the working electrode located in a cavity and electrically coupled to a recorder/integrator, wherein the working electrode and the cavity are dimensioned such that all parts of the cavity are located within a distance of the working electrode on the order of the diffusion layer thickness for the stationary solution.

6. An analyser according to claim 5, wherein the said distance is 0.015 cm or less.

7. An analyser according to claim 5, wherein the analyser defines an elongate rectangular section cavity, one side of which supports the working electrode.

8. An analyzer according to claim 5, wherein the analyser defines a tubular cavity the inner wall of which defines the working electrode.

9. An analyser according to claim 5, wherein the reference and any other electrode is located remote from the cavity.

10. An analyser according to claim 5, wherein the cavity defines a channel through which the solution is caused to flow, the working electrode being located within the channel such that the working electrode is spaced from at least an inlet end of the channel.

11. The analyser of claim 5, wherein the counter electrode in communication with the working electrode.

12. The analyser of claim 5, further comprising means for introducing a first sample of the solution into the cavity.

13. The analyser of claim 12, further comprising means for replacing the first sample of the solution within the cavity with a second sample of the solution such that the cavity remains filled with solution during the replacement procedure.

* * * * *